(12) United States Patent
Saini

(10) Patent No.: US 12,048,845 B2
(45) Date of Patent: Jul. 30, 2024

(54) METHODS OF FABRICATING IMPLANTABLE DEVICES

(71) Applicant: Teliatry, Inc., Richardson, TX (US)

(72) Inventor: Rahul Saini, Allen, TX (US)

(73) Assignee: Teliatry, Inc., Richardson, TX (US)

( * ) Notice: Subject to any disclaimer, the term of this patent is extended or adjusted under 35 U.S.C. 154(b) by 51 days.

(21) Appl. No.: 17/824,412

(22) Filed: May 25, 2022

(65) Prior Publication Data

US 2022/0288393 A1 Sep. 15, 2022

Related U.S. Application Data

(63) Continuation of application No. 16/948,720, filed on Sep. 30, 2020, now Pat. No. 11,364,385, which is a continuation of application No. 15/886,881, filed on Feb. 2, 2018, now Pat. No. 10,814,133.

(60) Provisional application No. 62/455,324, filed on Feb. 6, 2017.

(51) Int. Cl.
| | | |
|---|---|---|
| *A61N 1/375* | (2006.01) | |
| *A61N 1/36* | (2006.01) | |
| *A61B 5/00* | (2006.01) | |
| *A61B 5/24* | (2021.01) | |

(Continued)

(52) U.S. Cl.
CPC ....... *A61N 1/36071* (2013.01); *A61N 1/3605* (2013.01); *A61N 1/375* (2013.01); *A61B 5/24* (2021.01); *A61B 5/686* (2013.01); *A61B 5/6868* (2013.01); *A61B 5/6877* (2013.01); *A61B 2562/125* (2013.01); *A61N 1/0534* (2013.01); *A61N 1/0551* (2013.01);

(Continued)

(58) Field of Classification Search
CPC .... A61N 1/3605; A61N 1/375; A61N 1/3758; A61B 2562/125; Y10T 29/49126; Y10T 29/4913
See application file for complete search history.

(56) References Cited

U.S. PATENT DOCUMENTS

| | | |
|---|---|---|
| 5,095,905 A | 3/1992 | Klepinski |
| 5,215,088 A | 6/1993 | Normann et al. |
| 6,458,157 B1 | 10/2002 | Suaning |

(Continued)

FOREIGN PATENT DOCUMENTS

| | | |
|---|---|---|
| KR | 101159697 B1 | 6/2012 |
| KR | 20130091917 A | 8/2013 |

OTHER PUBLICATIONS

Bleiker, Simon J. et al., "Cost-Efficient Wafer-Level Capping for MEMS and Imaging Sensors by Adhesive Wafer Bonding", Micromachines, vol. 7, Issue 10, 2016, 12 pages.

(Continued)

*Primary Examiner* — Donghai D Nguyen
(74) *Attorney, Agent, or Firm* — Slater Matsil, LLP

(57) ABSTRACT

Implantable devices are provided herein, along with methods of fabricated such implantable devices. An exemplary method of fabricating an implantable device includes coupling electronics to a conductive via at a first side of a first glass substrate. The conductive via extends from the first side through the first glass substrate to a second side of the first glass substrate. The method further includes attaching a second glass substrate to cap the first side of the first glass substrate and form a hermetically sealed chamber containing the electronics, rounding edges of the implantable device after attaching the cap.

20 Claims, 14 Drawing Sheets

(51) Int. Cl.
     *A61N 1/05*      (2006.01)
     *A61N 1/372*     (2006.01)
(52) U.S. Cl.
     CPC ...... *A61N 1/36053* (2013.01); *A61N 1/36067* (2013.01); *A61N 1/37288* (2013.01); *A61N 1/3758* (2013.01)

(56) References Cited

U.S. PATENT DOCUMENTS

| | | | |
|---|---|---|---|
| 8,214,032 B2* | 7/2012 | Mech | H01L 23/29 |
| | | | 427/2.24 |
| 8,666,505 B2 | 3/2014 | O'Brien et al. | |
| 9,048,198 B2* | 6/2015 | Op De Beeck | A61N 1/37205 |
| 9,329,201 B2 | 5/2016 | Randall et al. | |
| 9,463,320 B2 | 10/2016 | Imran et al. | |
| 9,592,377 B2 | 3/2017 | Greenberg et al. | |
| 9,865,533 B2 | 1/2018 | Ruben et al. | |
| 10,772,228 B2* | 9/2020 | Day | H05K 5/0086 |
| 10,814,133 B2 | 10/2020 | Saini | |
| 2004/0006264 A1 | 1/2004 | Mojarradi et al. | |
| 2009/0301994 A1 | 12/2009 | Bhandari et al. | |
| 2011/0092842 A1 | 4/2011 | Decaria et al. | |
| 2011/0213443 A1 | 9/2011 | Greenberg et al. | |
| 2015/0329351 A1 | 11/2015 | Cheng et al. | |
| 2018/0029881 A1 | 2/2018 | Cheng et al. | |

OTHER PUBLICATIONS

European Search Report for PCT/US2018/016917 Mailing Date Oct. 29, 2020, 27 pages.

International Search Report and Written Opinion dated Jun. 26, 2018, International Application No. PCT/US2018/016917, 14 paqes.

Kim, S. et al., "Integrated wireless neural interface based on the Utah electrode array", Biomed Microdevices, vol. 11, 2009, pp. 453-466.

Ng, W. et al., "High-Q Si microresonators formed by substrate transfer on silica waveguide wafers", Optics Express, vol. 18, No. 26, Dec. 20, 2010, pp. 27004-27015.

\* cited by examiner

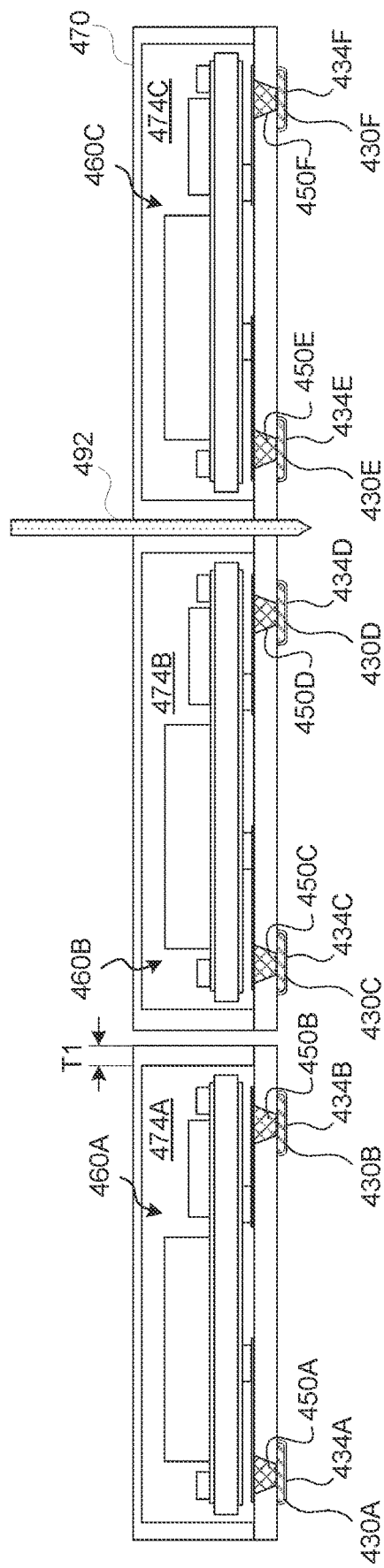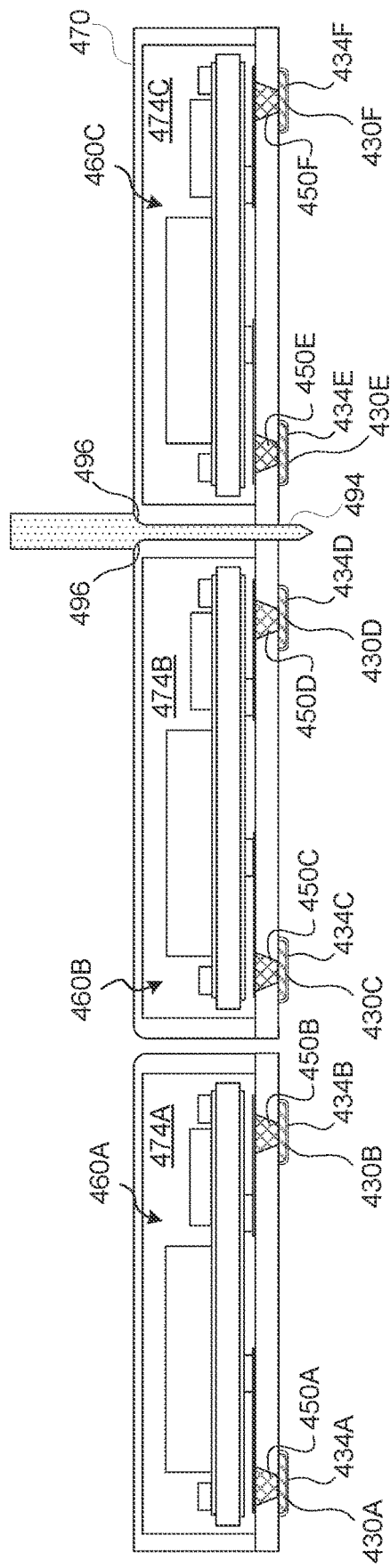

METHODS OF FABRICATING IMPLANTABLE DEVICES

CROSS-REFERENCE TO RELATED APPLICATIONS

This application is a continuation of U.S. application Ser. No. 16/948,720, filed on Sep. 30, 2020, which is a continuation of U.S. application Ser. No. 15/886,881, filed on Feb. 2, 2018, which claims the benefit of U.S. Provisional Application No. 62/455,324, filed on Feb. 6, 2017, which applications are hereby incorporated herein by reference in their entirety.

TECHNICAL FIELD

The present disclosure relates to neuromodulation and, more particularly, to devices, systems, and methods for electrically stimulating nerve(s), blocking nerve signaling, and/or monitoring nerve activity and to methods of fabricating such devices and systems.

BACKGROUND

Neuromodulation continues to increase as an adopted technique for treating of a wide variety of medical conditions. For example, neuromodulation devices for spinal cord stimulation have been utilized for the management of pain. Similarly, neuromodulation devices for deep brain stimulation have been utilized for the treatment of Parkinson's, essential tremor, dystonia, and other disorders. Neuromodulation devices for vagus nerve stimulation have been utilized to control seizures, such as those associated with epilepsy. Also, neuromodulation devices for renal nerve stimulation have been utilized to control blood pressure.

Neuromodulation devices typically require a surgical procedure to for implantation at a desired location within a patient. Because such devices are implanted, making the devices small is a concern. The use of microelectromechanical systems (MEMS) technology can aid in the production of devices that are small enough for implantation. Advances in fabrication of increasingly miniscule integrated circuit (IC) devices have coincided with advances in the use of semiconductors to form mechanical and electromechanical structures.

One promising application of MEMS devices includes the use of nano-scale and micro-scale electrodes formed on an IC substrate to measure and stimulate living tissue. The MEMS electrodes may be used to provide electrical stimulation and to measure electrical activity. These electrical potentials may represent sensory perception, muscular control, and other neural signals, and the electrodes may provide an avenue to restore lost neural function by stimulating targeted neurons. MEMS devices may also permit multiple components to be packages together to decrease the overall size of a device. However, the promised benefits have not yet been fully achieved. Accordingly, existing MEMS devices have been generally adequate but have not been entirely satisfactory in all respects.

As a result, there is a need for improved devices, systems, and methods for electrically stimulating nerves and/or monitoring nerve activity.

SUMMARY

The present disclosure relates to neuromodulation and, more particularly, to devices, systems, and methods for electrically stimulating nerve(s), blocking nerve signaling, and/or monitoring nerve activity and to methods of fabricating such devices and systems.

One exemplary aspect includes a method of fabricating an implantable device. An embodiment of the method includes forming at least one opening through a first substrate, bonding the first substrate to a second substrate, removing a portion of the second substrate, patterning a semiconductor layer of the second substrate to define a semiconductor structure over each opening of the first substrate, depositing a first conductive material over each semiconductor structure, and depositing a second conductive material within each opening of the first substrate such that the second conductive material is electrically coupled to the semiconductor structure. Other embodiments of this aspect include corresponding computer systems, apparatus, and computer programs recorded on one or more computer storage devices, each configured to perform the actions of the method or cause one or more machines to perform the actions of the method.

Another exemplary aspect includes a method of fabricating a plurality of implantable devices. An embodiment of the method includes bonding a first wafer to a second wafer, the first wafer having a plurality of through-wafer features formed therethrough. The method further includes removing a portion of the second wafer, patterning a semiconductor layer of the second wafer to define a semiconductor structure over each of the plurality of through-wafer features in the first wafer, and depositing a first conductive material over each semiconductor structure. Other embodiments of this aspect include corresponding computer systems, apparatus, and computer programs recorded on one or more computer storage devices, each configured to perform the actions of the method or cause one or more machines to perform the actions of the method.

Yet another exemplary aspect includes an implantable nerve transducer. An embodiment of the implantable nerve transducer includes a plurality of semiconductor structures protruding from an exterior surface provided by a substrate and a plurality of conductors extending from the exterior surface of the substrate to an interior surface of the substrate and within a plurality of openings in the substrate. Each conductor electrically is coupled to one of the semiconductor structures. The embodiment of the implantable nerve transducer further including one or more electronic components electrically coupled to the semiconductor structures by the conductors and a cap bonded to the substrate to provide a sealed chamber. The sealed chamber contains the one or more electronic components. Other embodiments of this aspect include methods of forming an individual implantable nerve transducer and forming a plurality of implantable nerve transducers.

Additional aspects, features, and advantages of the present disclosure will become apparent from the following detailed description.

BRIEF DESCRIPTION OF THE DRAWINGS

FIGS. 4A, 4B, 4C, 4D, 4E, 4F, 4G, 4H, 4I, 4J, 4K, and 4L are a series of cross-sectional side views of a plurality of implantable nerve transducers as fabricated according to the flowchart of FIG. 3 and according to embodiments of the present disclosure.

Figure 1:
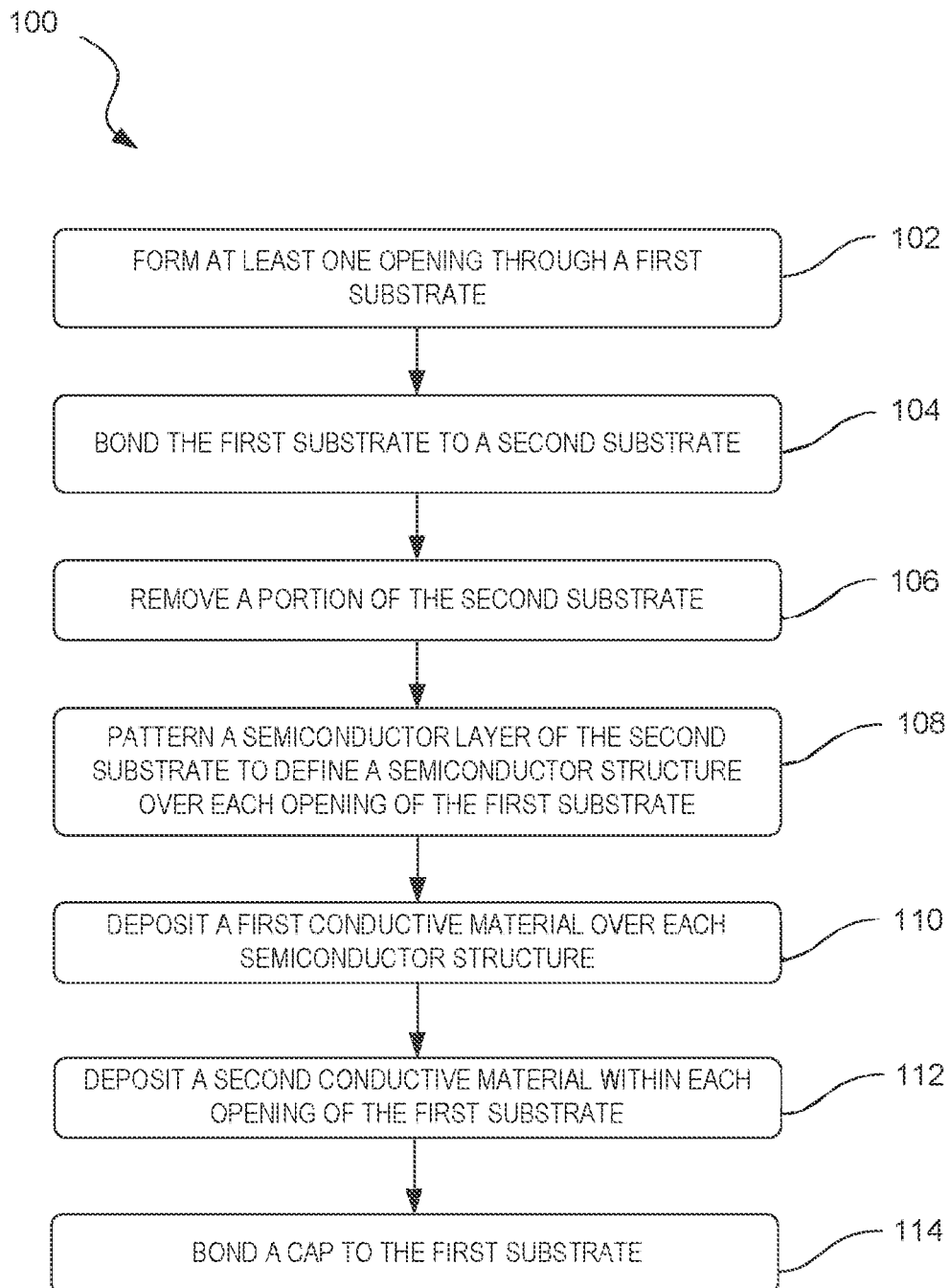
FIG. 1 is a flowchart of a method of fabricating an implantable nerve transducer according to embodiments of the present disclosure.

Theses drawings may be better understood by reference to the following detailed description.

DETAILED DESCRIPTION OF ILLUSTRATIVE EMBODIMENTS

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described methods, devices, and systems, and any further application of the principles of the present disclosure are fully contemplated and included within the present disclosure as would normally occur to one of ordinary skill in the art to which the disclosure relates. In particular, it is fully contemplated that the steps, features, and/or components described with respect to one embodiment may be combined with the steps, features, and/or components described with respect to other embodiments of the present disclosure. For the sake of brevity, however, the numerous iterations of these combinations will not be described separately.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. For example, if the device in the figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

FIG. 1 is a flowchart of a method 100 for fabricating an electrode for an implantable nerve transducer. The method 100 is illustrated as a series of enumerated steps or operations. Embodiments of the method 100 may include additional or alternative operations before, after, in between, or as part of the enumerated operations. Furthermore, some embodiments may not include all of the operations depicted in FIG. 1. In describing the method 100, reference is made to FIGS. 2A, 2B, 2C, 2D, 2E, 2F, and 2G.

Figure 2A:
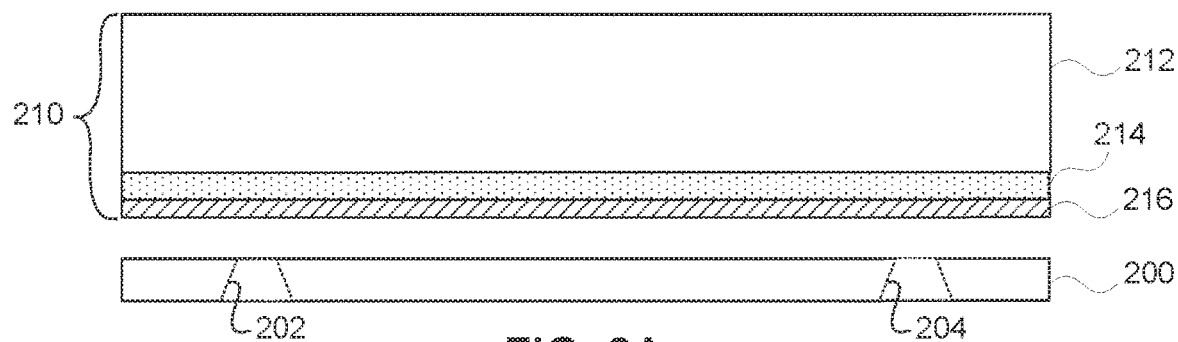
FIGS. 2A, 2B, 2C, 2D, 2E, 2F, and 2G are a series of cross-sectional side views of an implantable nerve transducer during fabrication according to the flowchart of FIG. 1 and according to embodiments of the present disclosure.

Accordingly, some embodiments of the method 100 may begin at operation 102, in which at least one through-wafer feature is formed in a first substrate. As shown in FIG. 2A, the first substrate 200 has a first hole or opening 202 formed therein as the at least one through-wafer feature. An additional opening 204 is also shown in FIG. 2A. Some embodiments of the first substrate 200 may include fewer or more openings formed therein. As illustrated, the openings 202 and 204 are tapered openings, such that the openings are larger on one side of the substrate 200 than on the other side. The openings 202 may be formed by mechanical drilling, etching, laser ablation, or another suitable process.

At operation 104, the first substrate is bonded to a second substrate. As shown in FIG. 2A, the second substrate 210 may include multiple layers of different materials. As shown in FIG. 2A, the second substrate 210 includes a handling layer 212, an intermediate layer 214, and a semiconductor layer 216. The handling layer 212 may be a silicon layer and the intermediate layer 214 may be a silicon oxide layer, such as a buried oxide layer. The semiconductor layer 216 may be a silicon layer as well. Accordingly, the second substrate 210 may be a semiconductor-on-insulator substrate or a silicon-on-insulator substrate. In some embodiments, the semiconductor layer 216 may be a doped semiconductor layer having dopants activated there so that the layer has a conductivity that is greater than the bulk material of the handling layer 212. The semiconductor layer 216 may range in size from about 10 µm to more than 100 µm. In the depicted embodiment, the semiconductor layer 216 is about 20 µm thick.

Figure 2B:
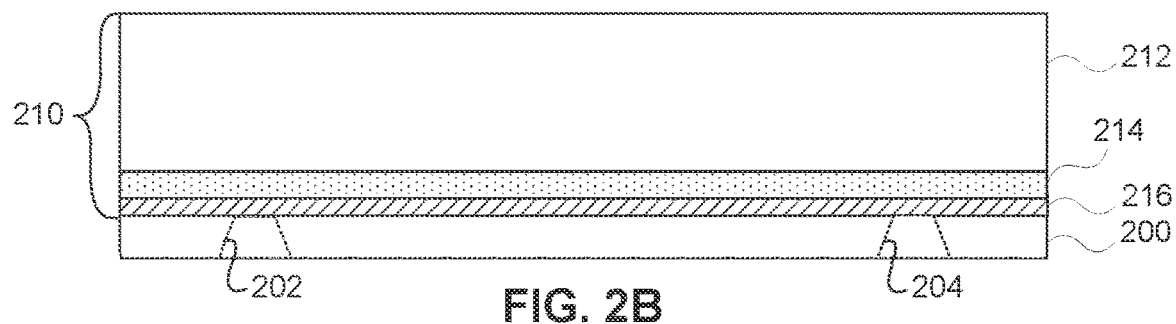

As shown in FIG. 2B, the second substrate 210 may be positioned in direct contact with the first substrate 200 so that the substrates 200 and 210 may be bonded together at operation 104. In order to bond the substrates 200 and 210, anodic bonding may be performed. To perform the anodic bonding, a first electrode may be coupled to the first substrate 200, while a second electrode is coupled to the second substrate 210. The substrates 200 and 210 may be heated and an electrostatic field may be applied using the first and second electrodes. The process seals the semiconductor layer 216 of the second substrate 210 to the first substrate 200 with a hermetic seal that may prevent bodily fluids from passing between the semiconductor layer 216 and the first substrate 200. In some embodiments, the first and second substrates 200 and 210 may be laser welded to form a hermetic seal between them. When the substrates 200 and 210 are laser welded, they may first be heated to about 100° C. and then annealed with a laser weld.

Figure 2C:
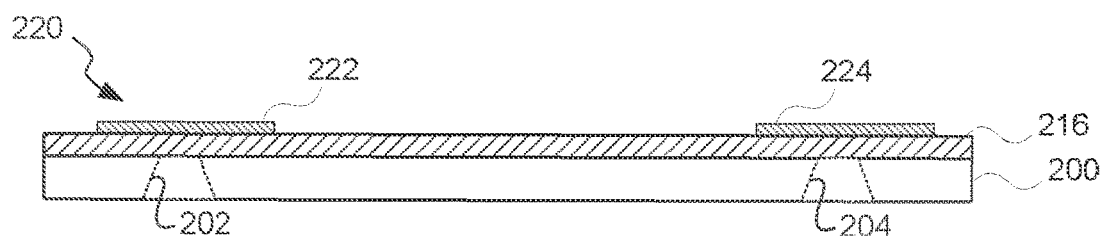

At operation 106, some of the material of the second substrate 210 may be removed. For example, a chemical-mechanical planarization (CMP) process may be performed to remove the handling layer 212 and the intermediate layer 214. In some embodiments, the handling layer 212 may be removed by a CMP process, while a chemical etch is used to remove the intermediate layer 214. The removal of material from the second substrate 210 may expose the unbonded surface of the semiconductor layer 216, as shown in FIG. 2C.

At operation 108, the semiconductor layer of the second substrate may be patterned to define a semiconductor structure over each opening in the first substrate. As shown in FIG. 2C, an etch mask 220 may be formed over the semiconductor layer 216. For example, a photoactive polymeric layer may be dispersed over the semiconductor layer 216 and patterned with a photolithographic process to produce mask features 222 and 224 in the etch mask 220. The mask features 222 and 224 may be positioned over the openings 202 and 204 formed in the first substrate 200. The openings 202 and 204 may be formed by a deep reactive ion etch process. For example, the ZERO-CROSSTALK™ DRIE process employed by Silex Microsystems, Inc. of Palo Alto, Calif. may be used to generate the openings 202 and 204, which may have tapered or straight profiles. Patterning the mask features 222 and 224 may include soft baking, mask aligning, exposure, post-exposure baking, developing the photoresist, rinsing, drying (e.g., hard baking), and/or other suitable photolithographic steps. Alternatively, the photolithographic process may be implemented, supplemented, or replaced by other methods such as maskless photolithography, electron-beam writing, and ion-beam writing. Thereafter, an etch process may be performed to remove the exposed portions of the semiconductor layer 216. For example, a deep reactive ion etching (DRIE) process may be performed on the exposed portions of the semiconductor layer 216. In other embodiments, another dry etch process or a wet etch process may be used to remove the exposed portions of the semiconductor layer 216.

Figure 2D:
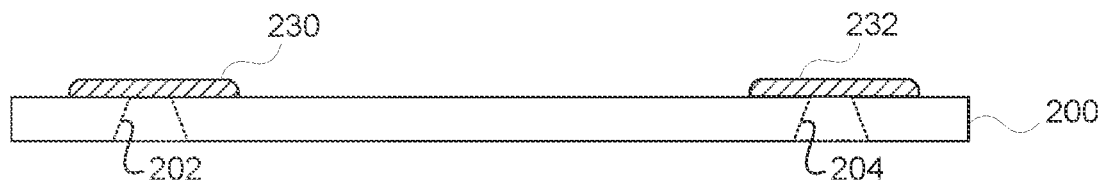

The etch process may be a chemically selective etch process, such that etching stops when the surface of the first substrate 200 is exposed. As shown in FIG. 2D, the mask features 222 and 224 may be removed from the remaining portions of the semiconductor layer 216. These remaining portions of the semiconductor layer 216 may be referred to as semiconductor structures. As shown in FIG. 2D, two semiconductor structures 230 and 232 remain on the surface of the first substrate 200. The patterning process performed at operation 108 may produce rounded edges on the upper surface of the semiconductor structures 230 and 232. As described, the semiconductor structures 230 and 232 are bonded to the first substrate 200 by the bonding process performed at operation 104. Accordingly, fluids, such as bodily fluids, are not able to pass between the semiconductor structures 230 and 232 and the underlying first substrate 200. The semiconductor structures 230 and 232 may be aligned with the openings 202 and 204, respectively. While two semiconductor structures 230 and 232 are shown in FIG. 2D, other embodiments may include more or fewer semiconductor structures.

Figure 2E:
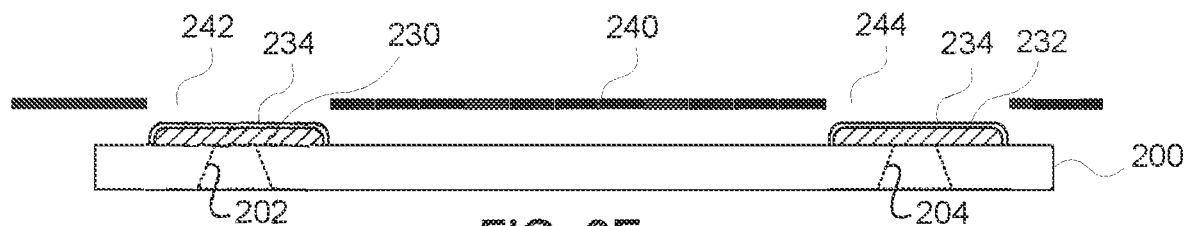

At operation 110, a first conductive material layer is formed over the exposed surfaces of each of the semiconductor structures 230 and 232, resulting in a conductive material layer 234 over the semiconductor structure 230 and a conductive material layer 236 formed over the semiconductor structure 232. The conductive material layers 234 and 236 may be produced by a shadow mask lithography process. The shadow mask lithography process may utilize a stencil or mask 240 as shown in FIG. 2E. The mask 240 may include windows 242 and 244 that correspond to the semiconductor structures 230 and 232 in size, shape, and position. A conductive material may be deposited over the substrate 200, being prevented by the mask 240 from being deposited in locations other than on the semiconductor structures 230 and 232 to form the conductive material layers 234 and 236. The conductive material contacts and adheres to the exposed surface of the semiconductor structures 230 and 232, and may seal the semiconductor structures 230 and 232 from exposure to bodily fluids when a device having the semiconductor structures 230 and 232 is implanted.

The conductive material may include biocompatible conductors including metals, metal nitrides, and conductive polymers. For example the conductive material layers 234 and 236 may be formed from materials such as copper, aluminum, tungsten, aluminum/silicon/copper alloy, titanium, titanium nitride, nickel, polysilicon, metal silicide, other metallic and non-metallic conductive materials, and/or combinations thereof and may have a multilayer composition. In some embodiments, a layer may be deposited over the semiconductor structures 230 and 232 and the exposed surface of the first substrate 200. The layer may be patterned by an etch process, leaving the layer over the semiconductor structures 230 and 232 as the first conductive material layers 234 and 236 The materials of the conductive material of the conductive material layers 234 and 236 may be deposited by one or more processes including sputtering, PVD, CVD, thermal annealing (commonly used to form metal silicides), photolithography, etching, and/or combinations thereof. In some embodiments, the conductive material layers 234 and 236 are made of titanium nitride (TiN). Other embodiments may include gold and/or platinum. For example, some embodiments may use an alloy of platinum and iridium as the material of the conductive material layers 234 and 236, while some other embodiments use an alloy of titanium, platinum, and gold.

Figure 2F:

At operation 112, a second conductive material is deposited over the opposite side of the first substrate 200, such that the second conductive material is deposited within each of the openings 202 and 204 and forms conductors or conductive vias 250 and 252. In some embodiments, the conductive material of the vias 250 and 252 is the same conductive material of the conductive material layers 234 and 236. In other embodiments, different conductive materials may be used instead. As shown in FIG. 2F, the vias 250 and 252 may entirely fill the space defined by the openings 202 and 204. However, in other embodiments the vias 250 and 252 are provided by a layer of conductive material that coats the walls of the openings 202 and 204 and coats the exposed portion of the semiconductor structures 230 and 232. The vias 250 and 252 may be formed using a shadow mask metallization process, similar to the process depicted in FIG. 2E, or by another appropriate fabrication process.

The vias 250 and 252 may be formed from materials such as copper, aluminum, aluminum/silicon/copper alloy, titanium, titanium nitride, tungsten, nickel, polysilicon, metal silicide, other metallic and non-metallic conductive materials, and/or combinations thereof and may have a multilayer composition. In an exemplary embodiment, the vias 250 and 252 include a nickel/aluminum alloy. The materials of the conductive material of the vias 250 and 252 may be deposited by one or more processes including sputtering, PVD, CVD, thermal annealing (commonly used to form metal silicides), photolithography, etching, and/or combinations thereof. In some embodiments, the vias 250 and 252 are made of titanium nitride. Other embodiments may include gold and/or platinum. For example, some embodiments may use an alloy of platinum and iridium as the material of the conductive material layers 234 and 236, while others use an alloy of titanium, platinum, and gold.

The vias 250 and 252 may be in direct physical contact with the semiconductor structures 230 and 232. Alternatively, another conductive material layer may be interposed therebetween. While a top surface of the vias 250 and 252 is illustrated as flush with the top surface of the first substrate 200, in FIG. 2F, some embodiments may include portions of the second conductive material protruding up from the surface of the first substrate 200, forming a lip thereon. In some embodiments, a brief chemical etch may be performed to remove any naturally occurring oxide on the exposed surface of the semiconductor structures 230 and 232 prior to depositing the material of vias 250 and 252 into the openings 202 and 204.

Figure 2G:
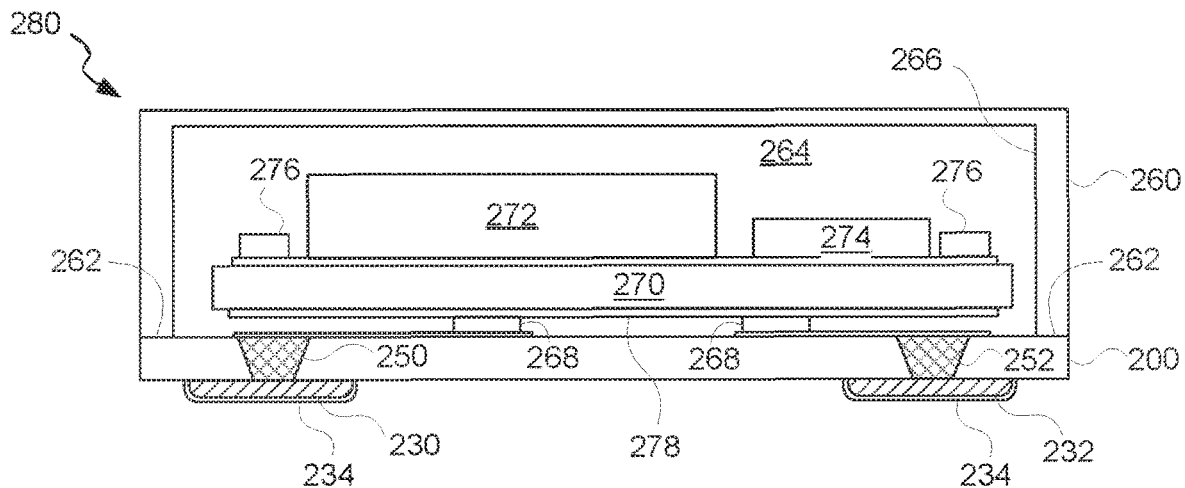

At operation 114, a cap may be bonded to the first substrate. As shown in FIG. 2G, a cap 260 is bonded to the first substrate 200 at surfaces 262 of the cap 260. The cap 260 may be made from glass, in some embodiments. Bonding may be accomplished by an anodic bonding process or by a laser welding process. As part of either bonding process, the cap 260 and the substrate 200 may be preheated, as in other bonding operations described herein. For example, the cap 260 and the substrate 200 may be preheated to a temperature of about 75° C. to about 150° C. Thereafter, an electrostatic charge may be placed across the cap 260 and the substrate 200, or the cap 260 and the substrate 200 may be exposed to laser activation or welding in a region corresponding to the surfaces 262. The bonding may hermetically seal a chamber 264, defined by a recess 266 and by an upper surface of the first substrate 200.

Prior to bonding the cap 260 to the first substrate 200, one or more electronic components may be positioned within the chamber 264 and electrically coupled to the vias 250 and 252 by leads 268. The electronic components may include a printed circuit board (PCB) 270, a microcontroller 272, a communication module 274, and other components 276. The printed circuit board 270 may route signals among and between the vias 250 and 252 (and the semiconductor structures 230 and 232), the microcontroller 272, the communication module 274, and/or the other components 176.

In some embodiments, the printed circuit board 270 may also support a coil structure 278. The coil structure 278 may be a coil of conductive material that is configured to wirelessly receive electromagnetic energy from a remote power source, such as a power source that is disposed outside of a patient's body. For example, when the implantable device 280, which includes the first substrate 200 and at least all of the features described as coupled thereto, electrically or mechanically, is implanted within a patient, the coil structure 278 may receive electromagnetic energy from a source disposed in proximity to the implantable device 280 but outside the patient's body. The other components 276 include resistors, capacitors, inductors, and may include one or more energy storage capacitors. The energy received by the coil structure 278 may charge an energy storage capacitor to provide power when the coil structure 278 is not receiving electromagnetic energy from an outside source.

Figure 2H:
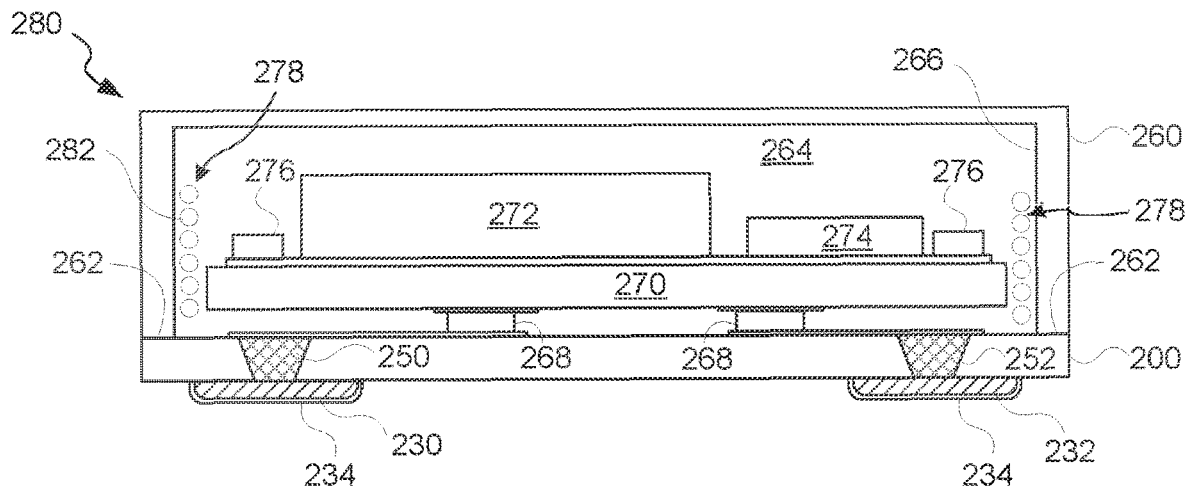
FIGS. 2H and 2I cross-sectional side views of alternative embodiments of the implantable nerve transducer of FIGS. 2A-G according to embodiments of the present disclosure.

As shown in FIG. 2G, the coil structure 278 may be a planar coil structure disposed on a surface of, or in a layer of, the printed circuit board 270. In other embodiments, the coil structure 278 may be disposed within the chamber 264 surrounding the printed circuit board 270 and the electronic components there on. As shown in FIG. 2H, the coil structure 278 is provided by a coiled wire 282 that wraps around the printed circuit board 270 repeatedly. While the coil structure 278 is shown as surrounding the printed circuit board 270, other embodiments of the coil structure 278 may be disposed above the printed circuit board 270 such that a lateral distance between the printed circuit board 270 and the walls of the recess 266 may be minimized.

Figure 2I:
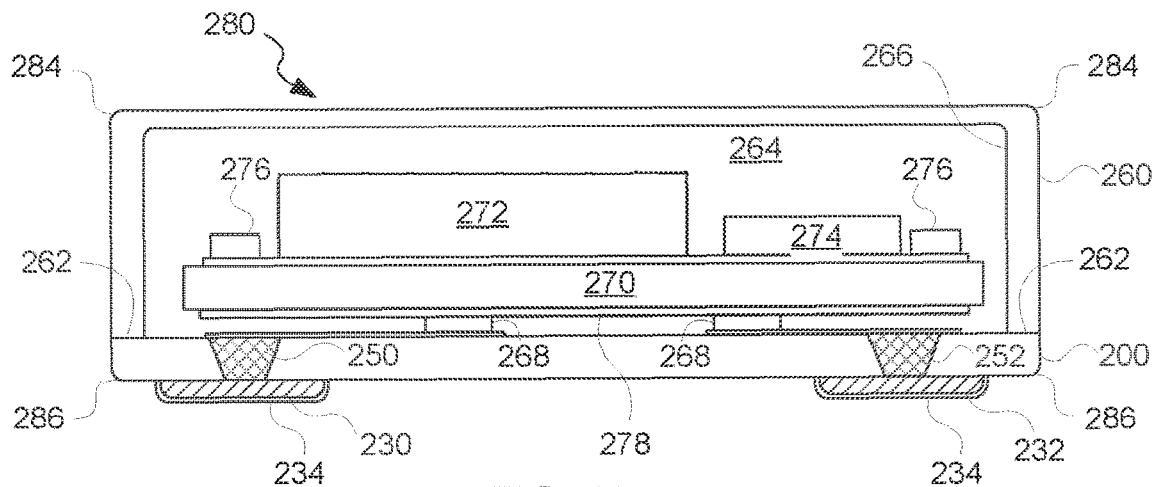

Before the implantable device 280 is positioned within a patient during a surgical procedure, the exterior corners or edges of the implantable device 280 may be smoothed or rounded. As shown in FIG. 2I, the exterior edges 284 of the cap 260 are rounded and the exterior edges 286 of the first substrate 200 are also rounded. The rounded edges 284 and 286 may be produced during a fabrication process used to individuate implantable devices that are formed in parallel, such as by wafer-level fabrication. The rounded edges 284 and 286 may be produced by a dicing process and/or an etching process, to reduce any impact the implantable device 280 may have on surrounding tissues at the site of implantation.

Figure 2J:
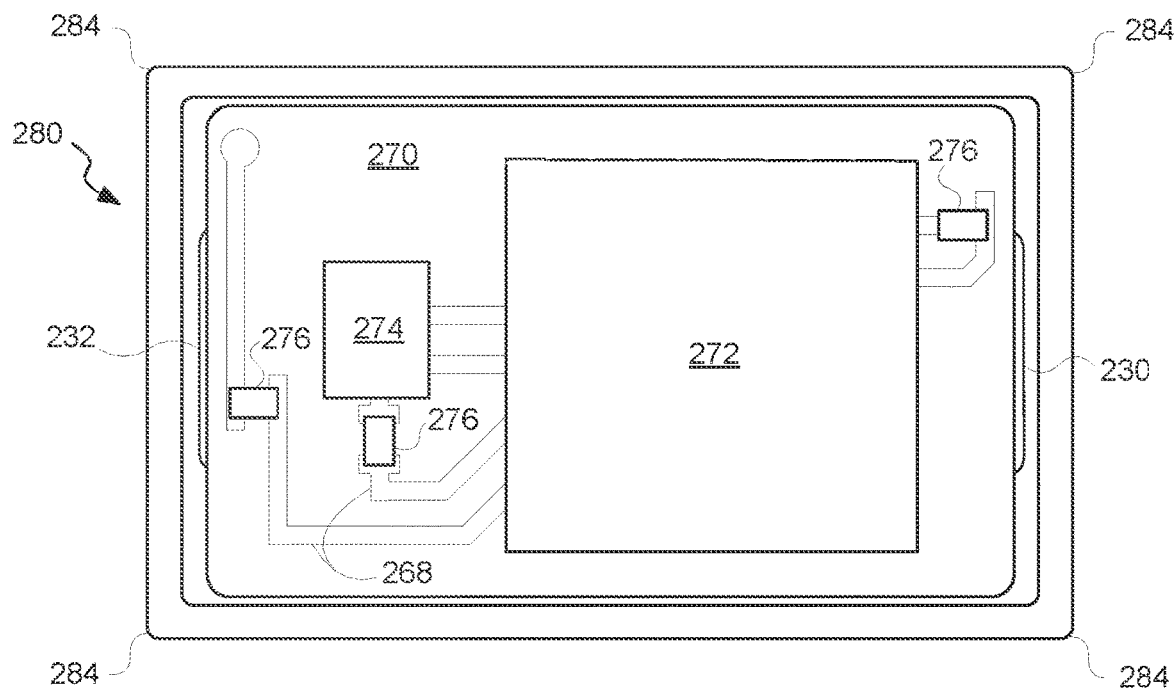
FIG. 2J is a diagrammatic, partial cross-sectional top view of an implantable nerve transducer according to embodiments of the present disclosure.
Figure 2K:
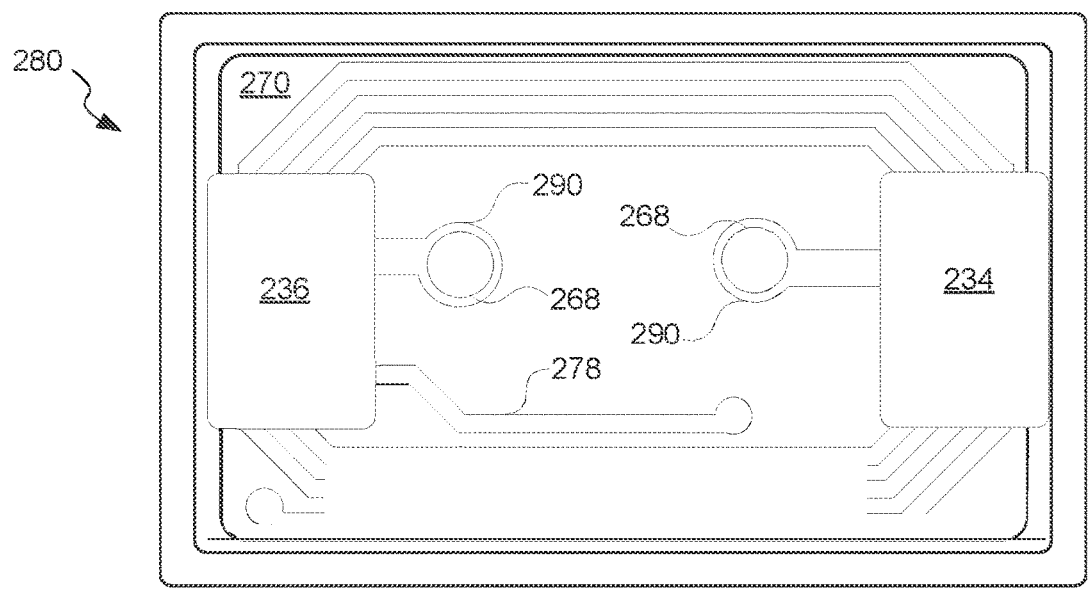
FIG. 2K is a diagrammatic, partial cross-sectional bottom view of an implantable nerve transducer according to embodiments of the present disclosure.

FIGS. 2J and 2K depict the implantable device 280 and partial cross section and a top view and a bottom view, respectively. FIG. 2J shows the microcontroller 272, the communication module 274, and other components 276 positioned on the printed circuit board 270. The top surface of the printed circuit board 270 may include leads 268. Additional leads may be included within the layers of the printed circuit board 270. The microcontroller 272 may include processing circuitry and radiofrequency communication circuitry to process information for transmission via the communication module 274 and to process information received via the communication module 274. In some embodiments, the communication module 274 is a near-field communication (NFC) module. In other embodiments, the communication module 274 may be configured to communicate in one or more other wireless protocols and associated frequencies, e.g., WLAN, Bluetooth, ZigBee, WiFi, etc. In some instances, both power and data are transmitted using radiofrequency (RF) communication. When both power and data are transmitted using RF communication, the RF communications for the power and data may be at different wavelengths. Additionally, in some embodiments, the power and/or data are transmitted using infrared (IR) communication and the communication module 274 may be an optical transceiver. In yet other embodiments, the power and data are transmitted using different communication techniques (e.g., RF communication for one and infrared (IR) communication for the other).

The microcontroller 272 may include a processor, a memory, a transceiver, and an antenna. These elements may be in direct or indirect communication with each other, for example via one or more buses. The processor of the microcontroller 272 may include a CPU, a DSP, an ASIC, a controller, a FPGA device, another hardware device, a firmware device, or any combination thereof. The microcontroller 272 may also be implemented as a combination of computing devices, e.g., a combination of a DSP and a microprocessor, a plurality of microprocessors, one or more microprocessors in conjunction with a DSP core, or any other such configuration.

The memory of the microcontroller 272 may include a cache memory (e.g., a cache memory of the processor), RAM, MRAM, ROM, PROM, EPROM, EEPROM, flash memory, a solid state memory device, one or more hard disk drives, other forms of volatile and non-volatile memory, or a combination of different types of memory. In an embodiment, the memory includes a non-transitory computer readable medium. The memory may store instructions. The instructions may include instructions that, when executed by the processor, cause the processor to perform operations to receive instructions and commands and to transmit data including status information and physiological data. Instructions may also be referred to as code, which may be interpreted broadly to include any type of computer-readable statement(s).

For example, the microcontroller 272 may receive and process signals from the semiconductor structures 230 and 232 to generate physiological data based on contact with nerves or nerve bundles. The microcontroller 272 may encode the physiological data for transmission by the communication module 274. Additionally, the communication module 274 may receive programming instructions and wireless signals and provide those programming instructions to the microcontroller 272 for reprogramming. The microcontroller 272 may include one or more memories for storing instructions and for storing physiological data.

FIG. 2K depicts a partially cross-sectioned bottom view of the implantable device 280. As shown in FIG. 2K, the coil structure 278 is disposed on a bottom surface of the printed circuit board 270. The semiconductor structures 230 and 232 are shown as enclosed in the conductive material layers 234 and 236, respectively. The semiconductor structures 230 and 232 are connected by planar conductors 290 to the leads 268. When implanted within a patient, the implantable device 280 is positioned so that electrodes (e.g., the semiconductor structures 230 and 232 and the conductive material layers 234 and 236) are in contact with one or more nerves or nerve bundles within the patient. Such nerves or nerve bundle include the spinal cord, the deep brain, vagus nerves, renal nerves, peripheral nerves, etc. Electrical impulses may be transmitted via the electrodes to the nerves and electrical impulses being transmitted via the nerves may be read using the electrodes.

Figure 2L:
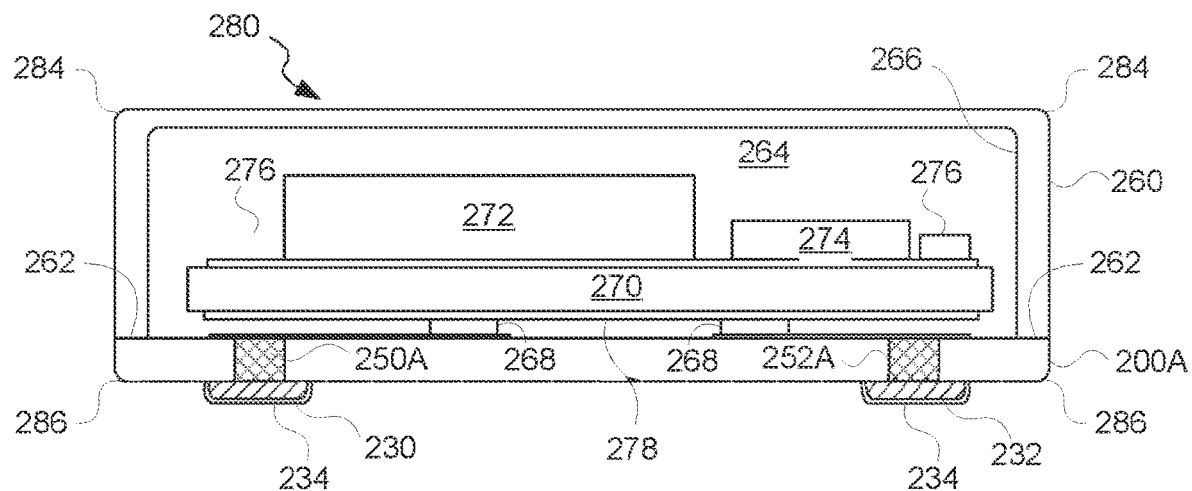
FIG. 2L is a cross-sectional side view of the implantable nerve transducer of FIGS. 2A-G according to embodiments of the present disclosure.
Figure 2M:
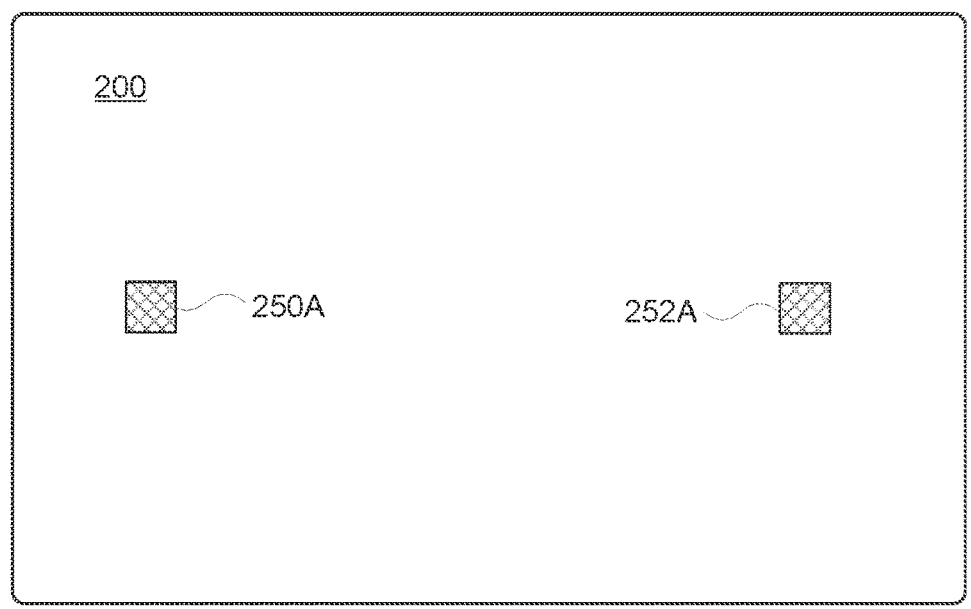
FIGS. 2M, 2N, and 2O are bottom views of a substrate includes vias according to embodiments of the present disclosure.
Figure 2N:
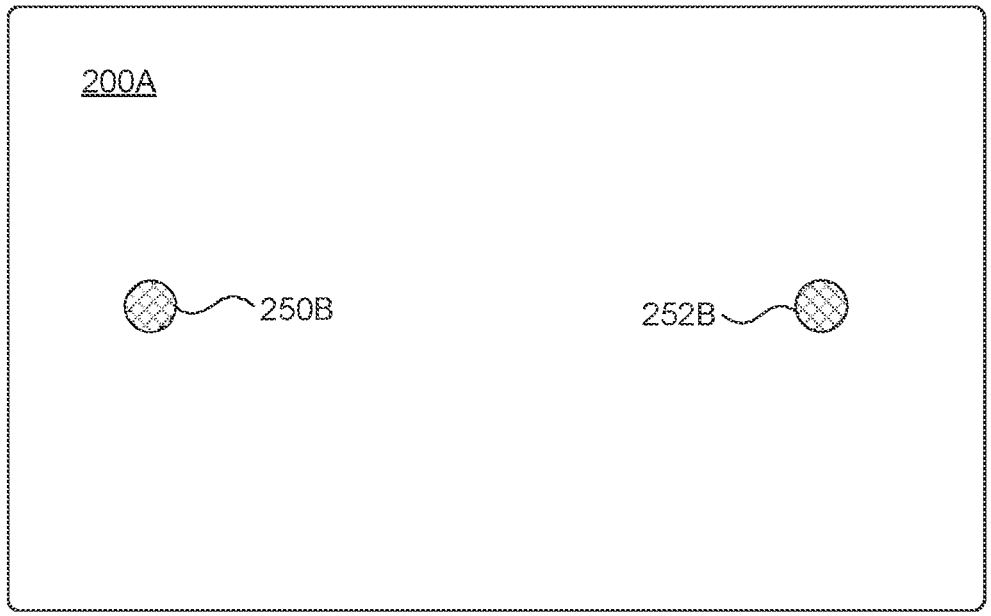
Figure 2O:
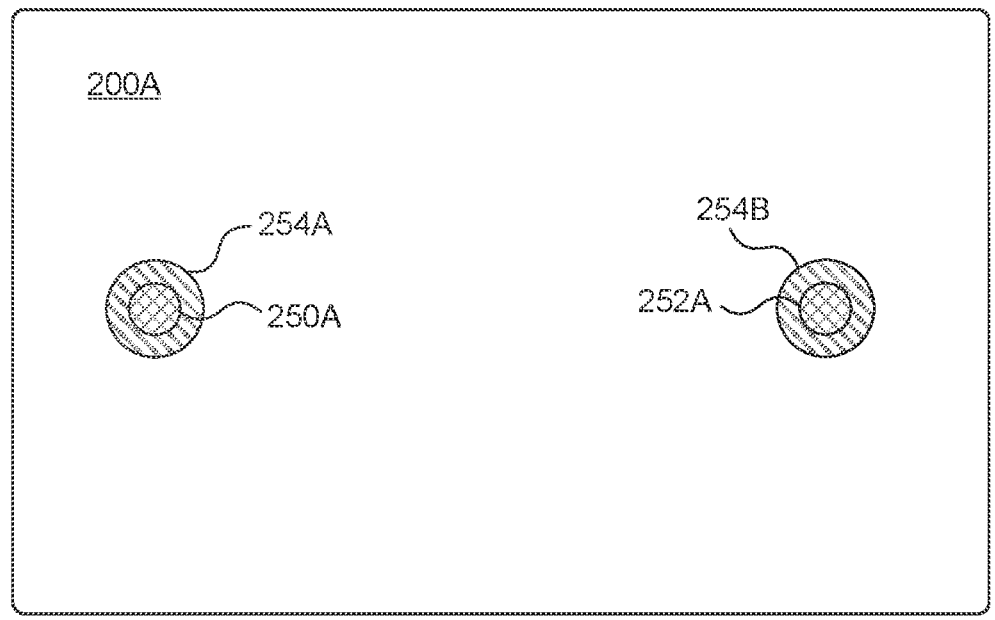

Referring now to FIG. 2L, shown therein is an embodiment of the implantable device 280 that includes an alternative first substrate 200A. The substrate 200A may be similar to the substrate 200 in many respects. For example, the bulk of the substrate 200A may include or be formed from a non-conductive material, such as an insulator. Additionally, the substrate 200A includes at least one through-wafer structure. The substrate 200A further includes alternative vias 250A and 252A as through-wafer structures. Accordingly, as used herein, a through-wafer structure may be an opening made in preparation for a conductive material to be formed therein to create a via or a through-wafer structure may be a formed via, including an opening filled with a conductive material. Rather than the tapered configuration of the vias 250 and 252 as shown in FIG. 2A, the vias 250A and 252A may be substantially straight through the bulk of the substrate 200A by being formed in openings that are substantially straight. The vias 250A and 252A may have a rectangular cross-sectional area, as shown in FIG. 2M, or a circular cross-sectional area, as shown in FIG. 2N. Both FIGS. 2M and 2N depict embodiments of the alternative substrate 200A from a bottom view. As illustrated, the substrate 200A has already been diced from a larger wafer. FIG. 2O depicts yet another embodiment of the alternative substrate 200A. The substrate 200A shown in FIG. 2O includes the alternative vias 250A and 252A and further includes isolation regions 254A and 254B. While the vias 250A and 252A are conductive, the isolation regions 254A and 254B provide for isolation between the vias 250A and 252A and the bulk material of the substrate 200A.

For example, the alternative substrate 200A may be made from bulk silicon, while the isolation regions 254A and 254B are formed from silicon oxide and the vias 250A and 252A are formed from doped polysilicon. Other materials may be used, however the vias 250A and 252A are more conductive than the bulk material of the substrate 200A, which is more conductive than the material of the isolation regions 254A and 254B. Additionally, the isolation regions 254A and 254B may have a different shape depending on, or independent of, the shape of the vias 250A and 252A.

When one of the alternative substrate 200A is used in fabrication of the implantable device 280, the method 100 of fabrication may omit operation 102. The operations involved with forming the vias 250 and 252 may also be omitted in the method, as the vias 250A and 252A may be formed before the electronic components (including the printed circuit board (PCB) 270, the microcontroller 272, the communication module 274, and other components 276) are bonded to the substrate 200A and before the alternative substrate 200A is bonded to the cap 260.

Some suitable embodiments of the substrate 200A may be SCHOTT HermeS® products from SCHOTT AG of Landshut, Germany, through glass via products made by Tecnisco, LTD. of Tokyo, Japan, and through glass via products made by Plan Optik AG of Elsoff, Germany.

Figure 3:
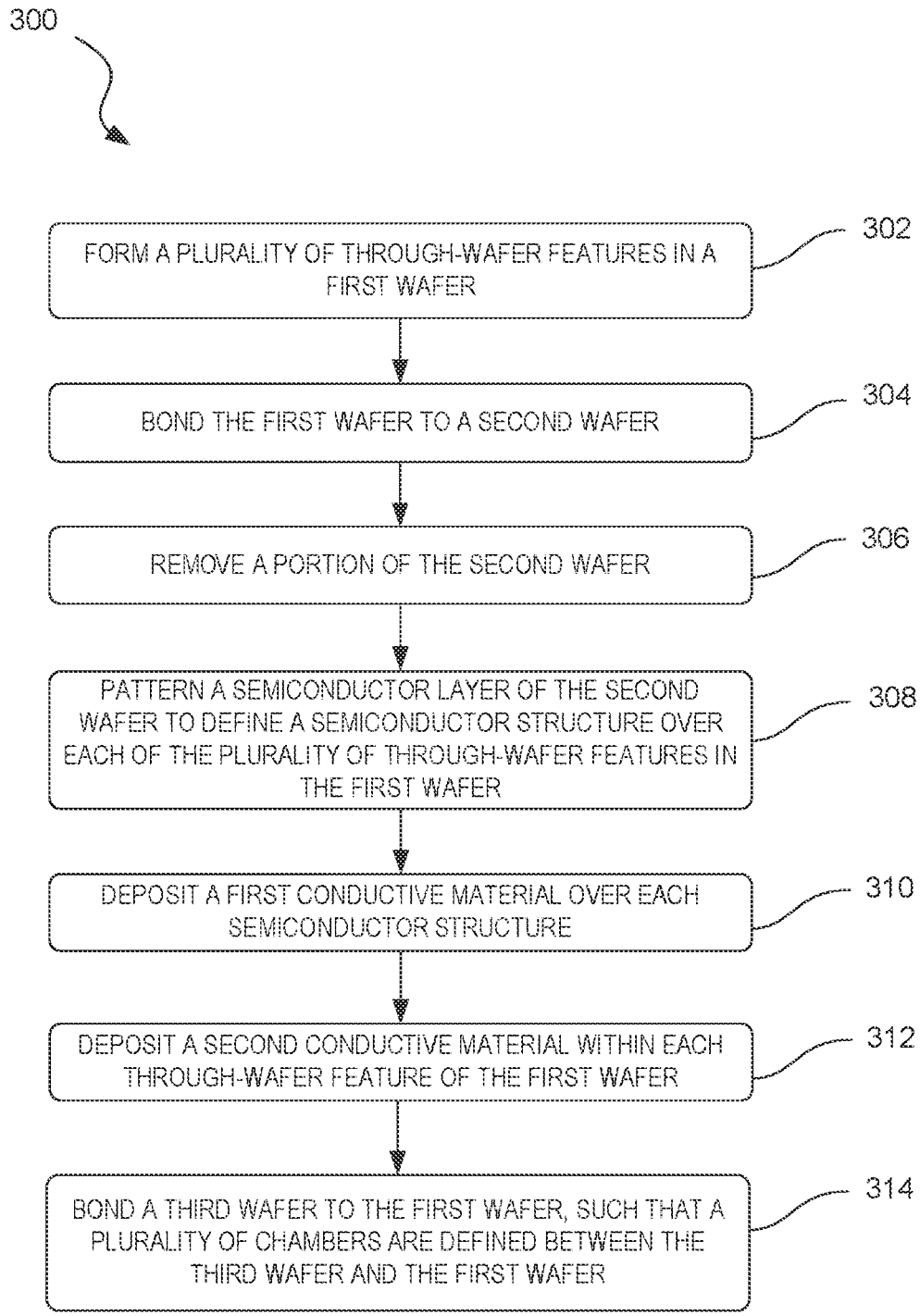
FIG. 3 is a flowchart of a method of wafer-level fabrication of a plurality of implantable nerve transducers according to embodiments of the present disclosure.

Referring now to FIG. 3, shown therein is a flowchart of a method 300 of fabricating a plurality of implantable devices, like the implantable device 280 of FIGS. 2G-2K. Like the method 100 of FIG. 1, method 300 is illustrated as a series of enumerated steps or operations. Embodiments of the method 300 may include additional operations before, after, in between, or as part of the enumerated operations. Additionally, some embodiments of the method 300 may omit one or more of the enumerated operations.

Figure 4A:
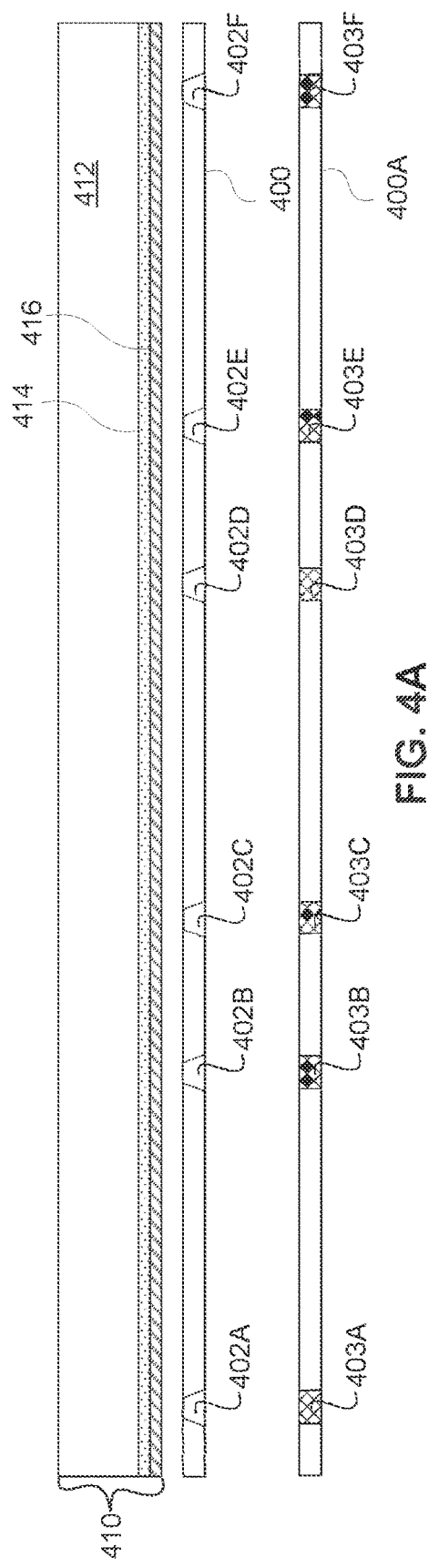

Accordingly, some embodiments of the method 300 may begin at operation 302, in which a plurality of through-wafer features is formed in a first wafer. FIG. 4A depicts a portion of a first wafer 400. The first wafer 400 may be machined, etched, or drilled to produce through-wafer features like the openings 402, which include individual openings 402A-F. The openings 402 may be tapered or straight. In the depicted embodiment of FIG. 4A, the openings 402 are tapered toward one end. FIG. 4A further illustrates an alternative first wafer 400A, which may take the place of the first wafer 400 in some embodiments of method 300. As discussed in connection with the substrate 200A of FIGS. 2L-2O, the first wafer 400 includes vias that differ from the vias formed in the openings 403A-F of first wafer 400 as shown in FIG. 4E, as discussed in further detail below. The vias 403A-F include a conductive material, such as a doped semiconductor or a metal, for conducting power and/or signals through the bulk material of the wafer 400A.

At operation 304, the first wafer may be bonded to a second wafer. As shown in FIG. 4A, the second wafer 410 may include a plurality of different material layers. In some embodiments, the second wafer 410 includes a handling layer 412, an intermediate layer 414, and a semiconductor layer 416 that separated from the handling layer 412 by the intermediate layer 414. In some embodiments, the handling layer 412 is silicon and the intermediate layer 414 is a buried oxide layer. Accordingly, the second wafer 410 may be referred to as a semiconductor-on-insulator wafer or a silicon-on-insulator wafer. While the individual thicknesses of the different material layers of the second wafer 410 may vary between embodiments, in some embodiments the semiconductor layer 416 may range from about 10 μm to about 100 μm. In some embodiments, the semiconductor layer is about 20 μm in thickness. Other embodiments of the method 300 may include a second wafer that has fewer material layers. For example, the second wafer 410 may be a silicon wafer without a buried oxide layer in some embodiments.

Figure 4B:
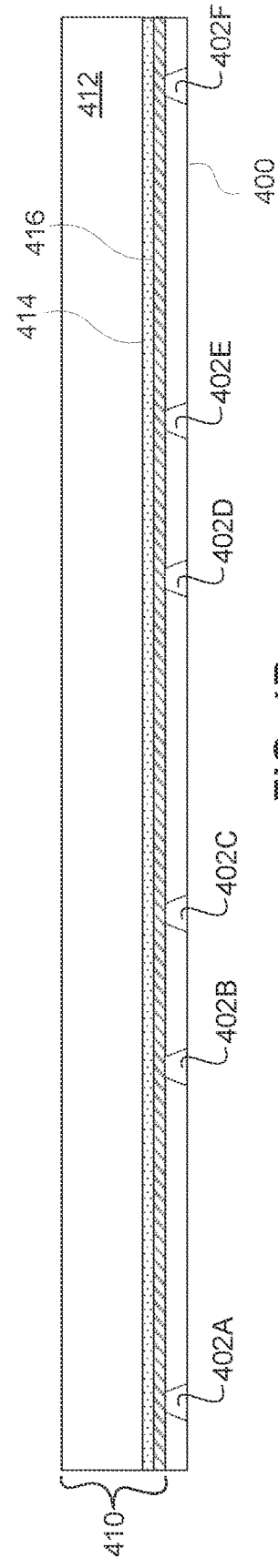

Bonding the first wafer 400 to the semiconductor layer 416 may produce the structure shown in FIG. 4B, which shows the combination of the bonded wafers 400 and 410. The first wafer 400 and the second wafer 410 may be bonded by anodic bonding or by laser welding as described herein to produce a hermetic seal between the first wafer 400 and the second wafer 410, more specifically between the first wafer 400 and the semiconductor layer 416.

Figure 4C:
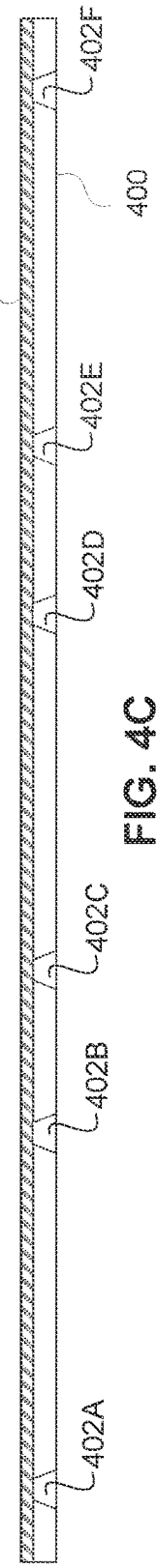

At operation 306, a portion of the second wafer is removed. As shown in FIG. 4C, the handling layer 412 and the intermediate layer 414 have been removed, exposing the semiconductor layer 416 which is bonded to the first wafer 400 with a hermetically sealed bond. Material may be removed from the second wafer 410 by chemical and/or physical processing steps, to provide a desired thickness for the semiconductor layer 416. As depicted in FIG. 4C, the semiconductor layer 416 has a generally constant thickness. In some embodiments of the operation 306, different thicknesses of material may be removed from the second wafer 410 in different locations, such that the thickness of the semiconductor layer 416 is different in different locations. Such embodiments may facilitate semiconductor structures with varying shapes and configurations, such as flat pads and needles of various heights and thicknesses.

Figure 4D:
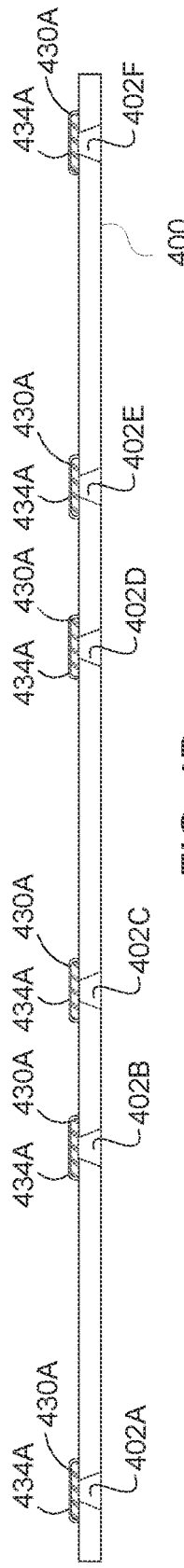
Figure 4E:
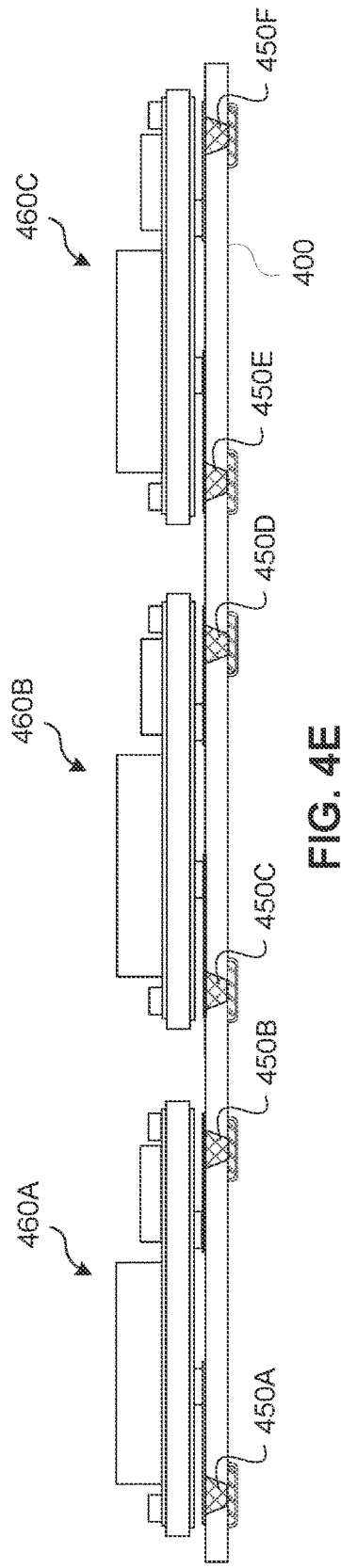

At operation 308, the semiconductor layer of the second wafer is patterned to define a plurality of semiconductor structures. This patterning may be performed using photolithographic techniques, such as the application and patterning of a layer of photoreactive material, such as photoresist, and subsequent etching of the exposed portions of the semiconductor layer 416. For example, the photoresist may be spun over the semiconductor layer 416 and exposed to produce mask features positioned over each of the openings 402 and the first wafer 400. For example, mask features like the mask features 222 and 224 of FIG. 2C may be formed over the openings 402, or another through-wafer feature in another embodiment. The exposed portions of the semiconductor layer 416 may be etched away, by a chemical etch that selectively etches the material of the semiconductor layer 416 faster than the material of the first wafer 400. The semiconductor layer 416 may be etched by a deep reactive ion etch process, in some embodiments. Alternatively or additionally, the physical etch may be used to pattern the semiconductor layer 416 into a plurality of semiconductor structures 430. FIG. 4D depicts six such semiconductor structures 430, labeled individually as semiconductor structures 430A-F. While all of the semiconductor structures 430 are depicted as being substantially planar, other embodiments of the operation 308 may include semiconductor structures 430 of varying configurations.

At operation 310, a first conductive material may be deposited over each semiconductor structure, the result of which is shown in FIG. 4D. Processes including formed by chemical vapor deposition (CVD), physical vapor deposition (PVD), atomic layer deposition (ALD), other suitable processes, and/or combinations thereof. In some embodiments, shadow mask lithography (depicted in FIG. 2E in connection with operation 110 of method 100) is used to selectively deposit the first conductive material in layers 434 (individual layers 434A-F) over each of the semiconductor structures 430. The first conductive material layers 434 may cover some, or all, of the exposed surface of the semiconductor structures 430. Accordingly, in some embodiments, the first conductive material layers 434 may provide an additional seal between the layers 434 and the first wafer 400, further preventing fluid from passing through the openings 402.

At operation 312, a second conductive material is deposited within the openings 402 in the first wafer. This may be done as shown in FIG. 2F and as described in connection with operation 112 of the method 100, to form vias 450 extending through the first wafer 400. The vias 450 are electrically coupled to the semiconductor structures 430 to transmit signals from a nerve or nerve bundle to one or more electronic components. The vias 450 may be in direct contact with a surface of each of the semiconductor structures 430 that is exposed by the openings 402. Chips 460 (individually, 460A-C) may be electrically and physically coupled to the vias 450 and the first wafer 400. The chips 460 may include a microprocessor, a communication module, a coil structure, and other components such as those depicted in FIGS. 2G and 2G, which are described therewith and, more generally, in connection with method 100 of FIG. 1. The chips 460 may be positioned by an automated pick-and-place machine to ensure proper placement and proper physical and electrical connection. Embodiments of the method 300 that including bonding the alternative wafer 400A to the second wafer 410 may omit operation 312. Alternatively, such embodiments may include operation 312 before operation 304.

Figure 4F:
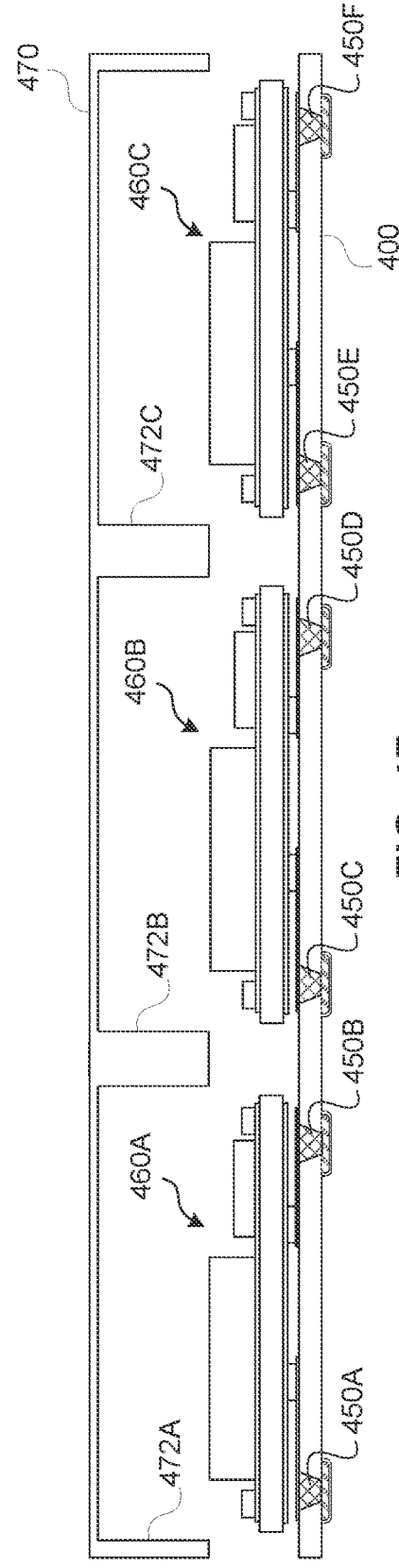
Figure 4G:
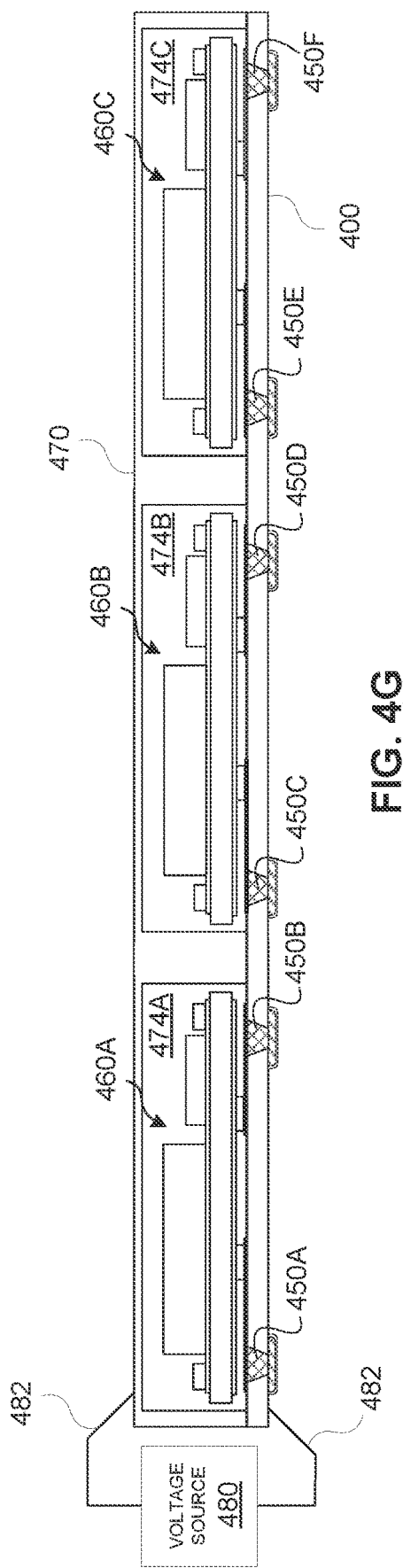

At operation 314, a third wafer is bonded to the first wafer, such that a plurality of chambers is defined between the third wafer on the first wafer. As shown in FIG. 4F, a portion of a third wafer 470 is shown while being positioned over the first wafer 400. The third wafer 470 includes a plurality of recesses 472, individually recesses 472A-C. When the wafer 400 and the third wafer 470 are in contact, a bonding process may be performed. As shown in FIG. 4G, a voltage source 480 may be coupled by electrodes 482 to the third wafer 470 and the first wafer 400. In some embodiments the voltage source 480 may be coupled to only one of the third wafer 470 and the first wafer 400, with the other connected to ground. Using the voltage source 480, an anodic bond may be formed between the wafers 400 and 470. The anodic bond seals chambers 474, defined by the recesses 472 and the upper surface of the first wafer 400, which include the chips 460.

Figure 4H:
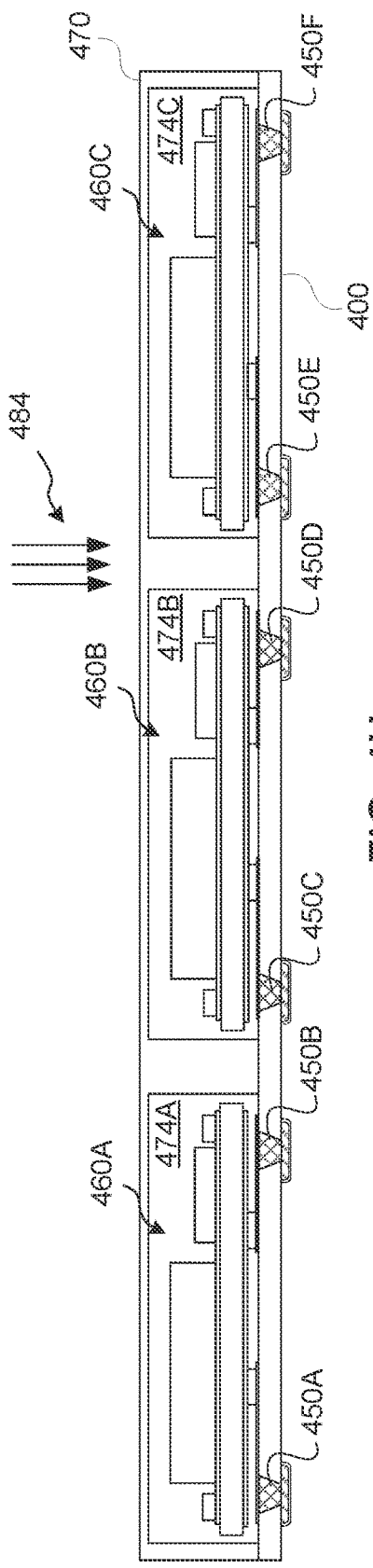

Alternatively, operation 314 may be performed by a laser welding process as depicted in FIG. 4H. As shown in FIG. 4H, the first wafer 400 and the third wafer 470 are brought into contact. The first wafer 400 and the third wafer for 70 may be heated or preheated to a temperature around 100° C. Thereafter, the wafers 400 and 470 may be exposed to a laser beam depicted by the arrows 484. The laser beam may be focused at the areas where the third wafer 470 contacts the first wafer 400. The laser beam may provide localized heat to the desired location of a bond. The laser beam may be directed across the wafer in a grid-like pattern to provide a seal that surrounds each of the chambers 474. Whether anodic bonding or laser beam welding is used, operation 314 results in hermetically sealed chambers 474.

Embodiments of the method 300 may further include one or more operations to divide the bonded wafers 400 and 470 into individual implantable devices, like the implantable device 280 described herein. Dicing the bonded wafers may be done using a dicing saw after attaching the wafer 400 or the wafer 470 to an adhesive carrier. Alternatively, a rotating bit may be used to separate the wafers into individual devices. FIG. 4I illustrates a dicing saw blade 492 that is separating an implantable device 490B from another implantable device 490C, which were produced in parallel by the wafer-level processing of method 300. After dicing, the walls of one of the implantable devices 490 may have a thickness T1 in a range from about 200 μm to about 600 μm. In some embodiments, the thickness T1 is about 500 μm. While the saw blade 492 has a uniform profile, other embodiments may include a saw blade 494 as illustrated in FIG. 4J. A rotating, dicing bit having the profile of the blade 494 may be used in some embodiments. The surface of the saw blade 494 includes a curve 496 on either side. These curves 496 operate to round the edges of the caps formed by the dicing of the third wafer 470, while the individual implantable devices 490 are being diced. As shown in FIG. 4J, the edges of the implantable device 490A have been rounded during the dicing process. The top edges between the implantable devices 490B and 490C are being rounded by the curves 496 while these devices are being separated by the dicing saw 494. In some embodiments, the dicing may be performed in two stages: once from a top surface and again from the bottom surface, with the blade not extending fully through both the wafers 400 and 470. While the illustrated examples in FIGS. 4I and 4J depict the saw blade as penetrating from the third wafer 470 to the first wafer 400, the saw blade 492 or 494 may also individuate the implantable devices 490 from the first wafer 400 to the third wafer 470.

Figure 4K:
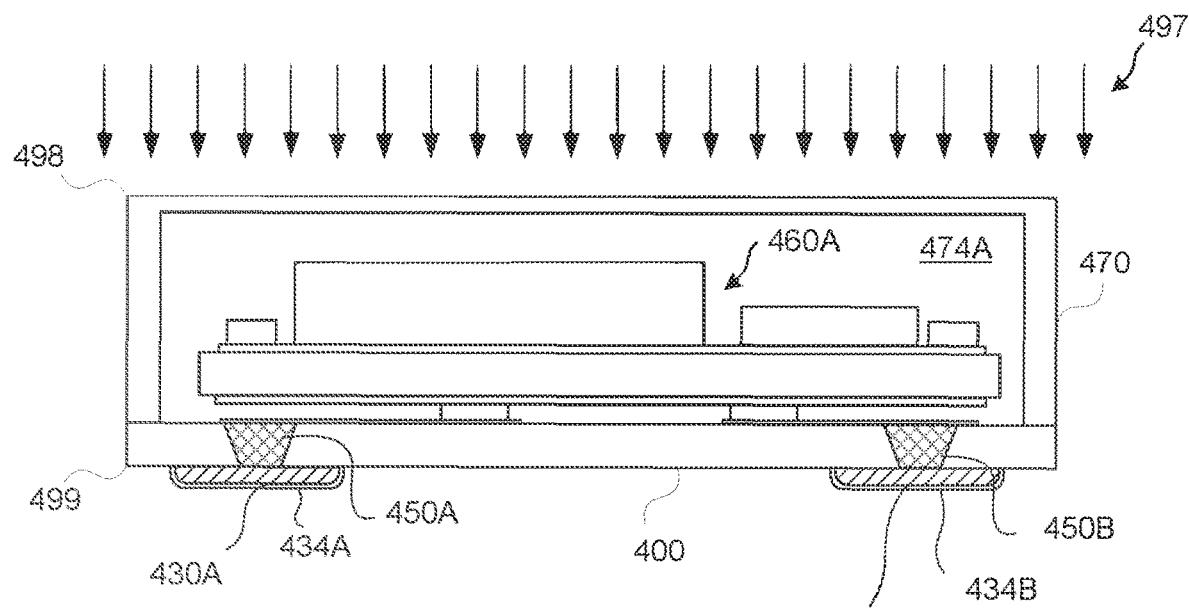
Figure 4L:
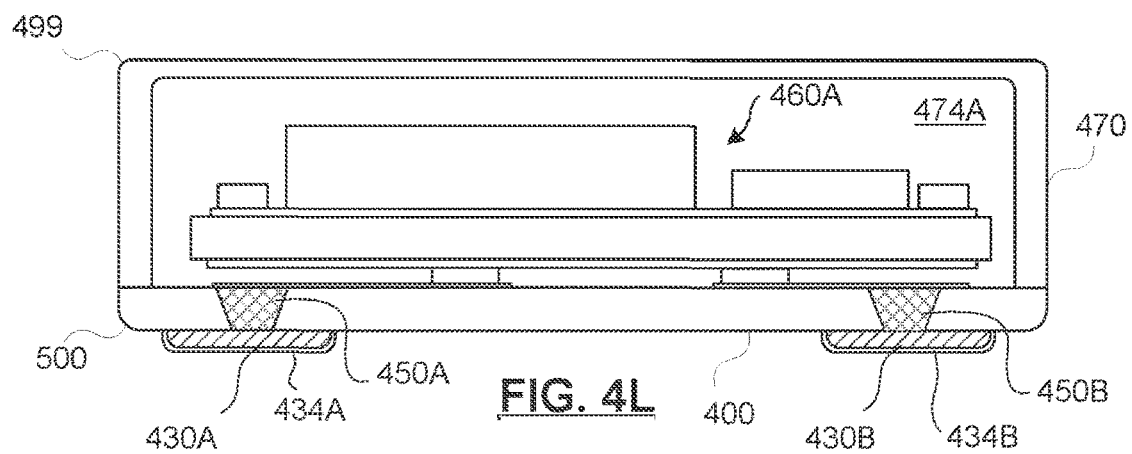

Alternatively or additionally, an etching process may be performed to round the corners of the implantable devices 490. For example, as shown in FIG. 4K, and etch process 497 may be performed to round the corners 498 to produce rounded corners 499 as depicted in FIG. 4L. In some embodiments of the method 300, a first etch process may be performed to round the top corners of the implantable devices 490 and a second etch process may be performed to round the bottom corners of the implantable devices.

Figure 5A:
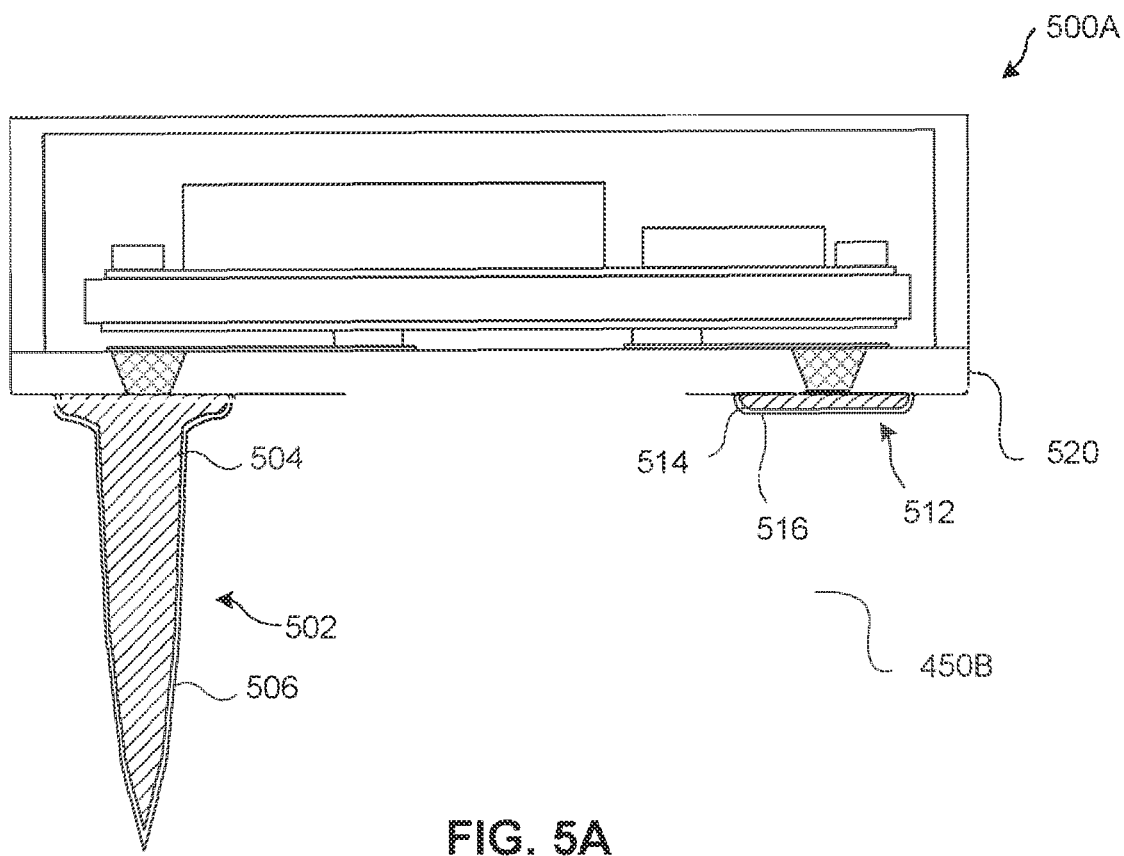
FIGS. 5A and 5B are cross-sectional side views of exemplary implantable nerve transducers having varying electrodes according to embodiments of the present disclosure.
Figure 5B:
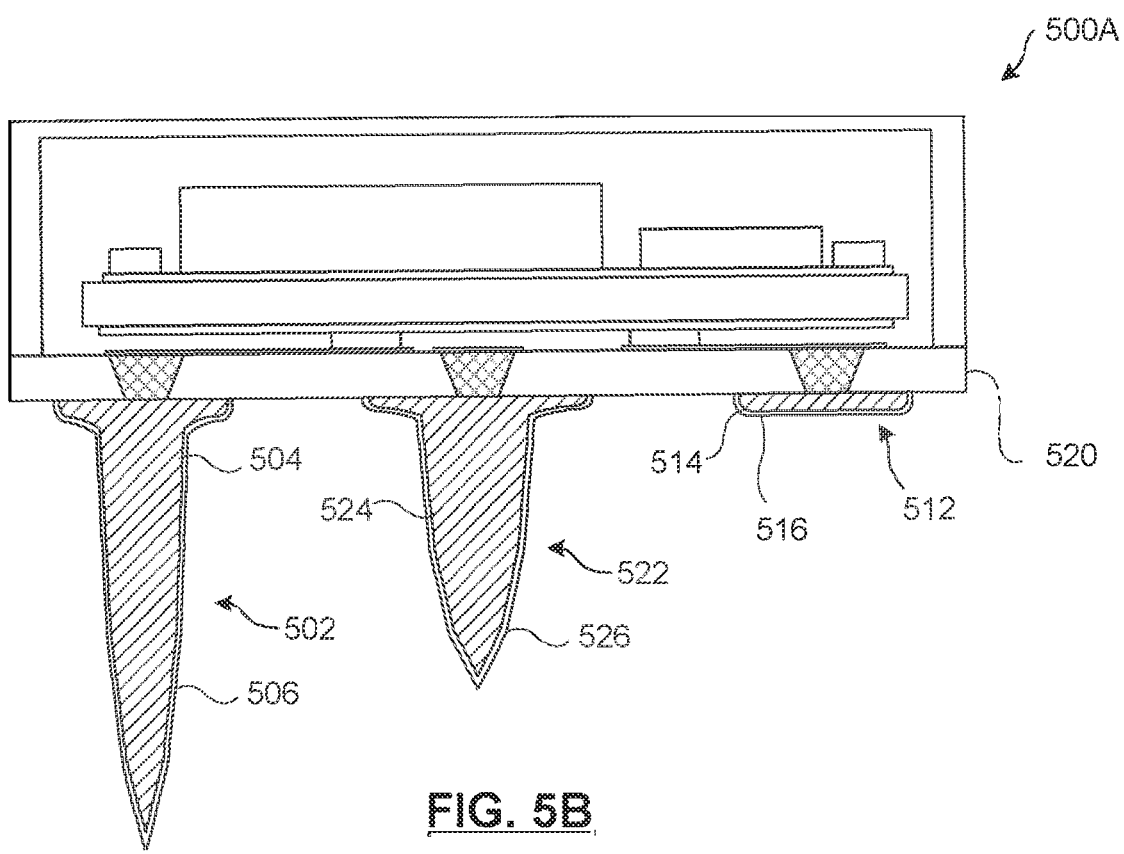

Referring now to FIGS. 5A and 5B, shown therein are implantable devices 500A and 500B, respectively. The implantable devices 500A and 500B may be formed by embodiments of the methods 100 and 300. This may be done by adding additional steps as part of the operation 108 of method 100 and operation 308 of method 300. These additional steps may be described in more detail in U.S. Pat. No. 9,329,201, filed on Mar. 13, 2014, and entitled "Methods, Devices, and Systems for Forming Atomically Precise Structures," the entire disclosure of which is incorporated herein by reference. As shown in FIG. 5A, the implantable device 500A includes a first electrode 502 and a second electrode 512. The first electrode 502 has a needle-like shape and may be referred to as a penetrating needle. The second electrode 512 has a generally planar shape and may be referred to as an electrode pad. Both of the electrodes 502 and 512 include a semiconductor structure, referred to as semiconductor structures 504 and 514, respectively. The semiconductor structures 504 and 514 may be formed from a single semiconductor layer that was bonded to the substrate 520. As noted herein, the semiconductor layer may have different heights or thicknesses at different locations. The electrodes 502 and 512 may also include a conductive coating thereon. As illustrated, the electrode 502 includes a coating provided by a conductive material layer 506. The electrode 512 includes a conductive material layer 516. In some embodiments, either or both of the electrodes 502 and 512 may include an insulating coating or layer having an opening to more precisely control where an electrical connection or connections may be made with the electrodes 502 and 512 by nerves or bundles of nerves.

FIG. 5B depicts an implantable device 500B that includes more than two electrodes. As described herein, the implantable devices made by the methods 100 and/or 300 may include one electrode, two electrodes, or more electrodes. The implantable device 500B includes the electrode 502 and the electrode 512, and further includes an electrode 522. Like the electrodes 502 and 512, the electrode 522 includes a semiconductor structure 524 and a conductive material layer 526 deposited thereon. As shown, the electrode 522 is shorter than the electrode 502 and taller than the electrode 512. Additionally, the electrode 522 is wider than the electrode 502.

In general, the implantable devices disclosed herein may include configured in a linear array, a two-dimensional array, or other suitable spatial distribution. The electrodes can be of various type, including penetrating electrodes, self-embedding electrodes (e.g., electrodes with a structural profile, such as an hourglass profile, that allows insertion into a nerve or nerve bundle, but resists or prevents unwanted removal without requiring a separate securing device, such as a tack), flat or surface electrodes, flexible electrodes, and/or combinations thereof. Further, in some instances each electrode may include a plurality of discrete stimulation and/or monitoring sites. In this regard, a penetrating needle with a plurality of discrete stimulation and/or monitoring sites at various positions along the length of the electrode can be utilized to precisely target stimulation and/or monitoring at a desired depth or combination of different depths of a nerve or nerve bundle. Such varied configurations of the exemplary electrodes 502, 512, and 522 may be employed to contact a nerve bundle at different depths or to contact different nerves using a single implantable device 500A or 500B.

Additional embodiments of implantable devices described herein may include electrodes with yet other different shapes and dimensions, as described in U.S. Pat. No. 9,329,201. The methods described herein produce implantable nerve transducers that are hermetically sealed to prevent any fluid from accessing electronic components encased within the implantable devices. The implantable devices may have biocompatible exterior materials to prevent complications during use of the devices. These devices may receive power wirelessly and may record neural activity and communicate recorded data wirelessly to a receiver outside the patient's body, through skin and other tissue.

As those of some skill in this art will by now appreciate and depending on the particular application at hand, many modifications, substitutions and variations can be made in and to the materials, apparatus, configurations and methods of fabrication of the devices of the present disclosure without departing from the spirit and scope thereof. In light of this, the scope of the present disclosure should not be limited to that of the particular embodiments illustrated and described herein, as they are merely by way of some examples thereof, but rather, should be fully commensurate with that of the claims appended hereafter and their functional equivalents.

What is claimed is:

1. A method of fabricating an implantable device, the method comprising:
   coupling electronics to a conductive via at a first side of a first glass substrate, the conductive via extending from the first side through the first glass substrate to a second side of the first glass substrate;
   attaching a second glass substrate as a cap of the first side of the first glass substrate to form a hermetically sealed chamber containing the electronics; and
   rounding edges of both the first glass substrate and the second glass substrate after attaching the cap.

2. The method of claim 1, wherein rounding the edges comprises rounding all exterior edges of the implantable device.

3. The method of claim 1, wherein rounding the edges comprises chamfered dicing to form obtuse angles at the edges.

4. The method of claim 1, wherein rounding the edges comprises machining the edges.

5. The method of claim 1, wherein the rounding is performed during a dicing process that dices through the first glass substrate and the second glass substrate.

6. The method of claim 1, wherein both the first glass substrate and the second glass substrate are borosilicate glass substrates.

7. A method of fabricating an implantable device, the method comprising:
   forming a through glass via extending from a first side of a glass substrate, through the glass substrate, to a second side of the glass substrate;
   coupling electronics to the through glass via at the first side of the glass substrate;
   forming a glass cap from another glass substrate, the glass cap comprising an opening;
   attaching the glass cap to the first side of the glass substrate to hermetically seal the opening and form a sealed chamber containing the electronics; and
   rounding all exterior edges of the implantable device after attaching the glass cap.

8. The method of claim 7, wherein attaching the glass cap comprises laser welding the glass cap to the first side of the glass substrate.

9. The method of claim 8, wherein laser welding the glass cap to the first side of the glass substrate comprises using a plurality of weld lines to laser weld the glass cap to the first side of the glass substrate.

10. The method of claim 7, wherein attaching the glass cap comprises anodic bonding of the glass cap to the first side of the glass substrate.

11. The method of claim 7, wherein rounding all of the exterior edges comprises chamfered dicing to form obtuse angles at all of the exterior edges.

12. The method of claim 7, wherein rounding all of the exterior edges comprises machining all of the exterior edges.

13. The method of claim 7, wherein the glass substrate is a borosilicate glass substrate.

14. The method of claim 7, wherein the glass cap is a borosilicate glass cap.

15. A method of fabricating implantable devices, the method comprising:
   coupling a plurality of electronic components to a plurality of conductive vias at a first side of a base substrate, the plurality of conductive vias extending from the first side through the base substrate to a second side of the base substrate;
   attaching a cap substrate to the first side of the base substrate to form a plurality of sealed chambers containing the plurality of electronic components, a first subset of the plurality of electronic components being in a first chamber and a second subset of the plurality of electronic components being in a second chamber;
   dicing the base substrate with the attached cap substrate to form a first implantable device comprising the first chamber and a second implantable device comprising the second chamber; and
   rounding edges of both the base substrate and the cap substrate for the first implantable device and the second implantable device, respectively.

16. The method of claim 15, wherein rounding the edges comprises chamfered dicing to form obtuse angles at the edges while dicing the base substrate with the attached cap substrate.

17. The method of claim 15, wherein rounding the edges comprises machining the edges.

18. The method of claim 15, further comprising:
   forming the cap substrate by attaching a bare glass substrate to a glass substrate with a plurality of holes therethrough.

19. The method of claim 15, further comprising:
   forming the cap substrate by machining recesses into a bare glass substrate.

20. The method of claim 15, wherein both the base substrate and the cap substrate are glass substrates.

* * * * *